United States Patent
Hebert

[19]

[11] Patent Number: 6,074,272
[45] Date of Patent: Jun. 13, 2000

[54] NURSING PAD BRA LINER

[76] Inventor: Carrie A. Hebert, 210 Dogwood Ave., Altus, Okla. 73521

[21] Appl. No.: 09/181,356

[22] Filed: Oct. 28, 1998

[51] Int. Cl.[7] .................................................. A41C 3/04
[52] U.S. Cl. .............................................. 450/37; 450/81
[58] Field of Search .................................. 450/37, 56, 55, 450/81; 128/890; 2/104, 56, 58, 267

[56] References Cited

U.S. PATENT DOCUMENTS

| | | | |
|---|---|---|---|
| 3,001,201 | 9/1961 | Hauser | 2/56 |
| 3,356,090 | 12/1967 | Plantinga et al. | 128/280 |
| 4,125,114 | 11/1978 | Repke | 604/366 |
| 4,674,510 | 6/1987 | Sneider | 450/57 |
| 4,700,699 | 10/1987 | Tollerud et al. | 604/358 |
| 4,747,162 | 5/1988 | Yanagihara | 2/53 |
| 4,875,492 | 10/1989 | Mitchell et al. | 128/890 |
| 5,326,305 | 7/1994 | Fochler | 450/57 |
| 5,683,286 | 11/1997 | Kielland | 450/37 |
| 5,919,180 | 7/1999 | Raimondo | 604/387 |

*Primary Examiner*—John J. Calvert
*Assistant Examiner*—Alissa L. Hoey
*Attorney, Agent, or Firm*—Robert Treece

[57] ABSTRACT

A nursing pad liner for placing against the breast of a woman and for placing against the clothing of the woman, the liner being of the type to avert fluid leaking from the woman from soiling the woman's clothing, said liner comprising a layer of adsorbent material having an outside and an inside to adsorb and hold at least some fluid leaking from a woman's breast when held there against and a liquid impermeable outer layer for covering the outside of the adsorbent material and extending inside partially around the adsorbent material to form a reservoir.

15 Claims, 1 Drawing Sheet

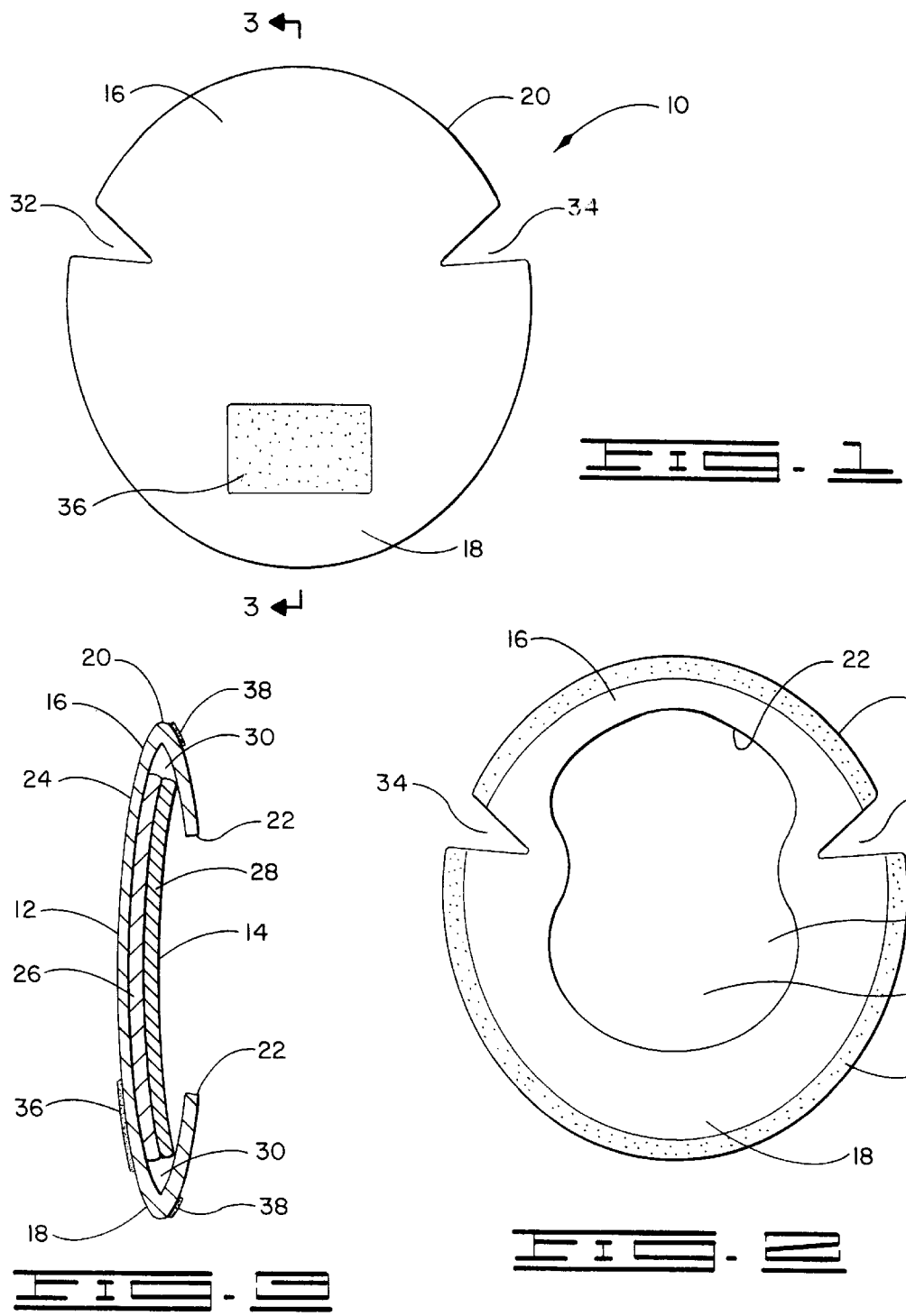

NURSING PAD BRA LINER

BACKGROUND OF THE INVENTION

1. Field of the Invention

The invention relates to bra liners. In particular the invention relates to bra liners for use by nursing mothers to prevent unwanted leakage of breast milk. The invention has a multilayered design including a non-permeable layer for preventing transfer of breast milk from the liner to clothing, an absorbent layer for holding the milk within the liner and a wicking layer to draw the liquid away from the breast and into the absorbing layer. A non-permeable layer is also disposed about the outer periphery of the liner so that a reservoir is formed between the outer surface non-permeable layer and the layer on the periphery for retaining excess milk. The design of the invention may incorporate cutouts along the periphery of the liner which allow the pad to more easily conform to the shape of a breast. An adhesive may be applied to the outer portion of the liner to hold the liner in place in the users bra cup. An adhesive may also be used to hold the liner to the users breast.

2. Description of the Prior Art

Devices for preventing breast milk leakage from contacting and seeping into and through clothing are currently available on the market. Generally, these devices fall into two broad categories: nursing or breast pads and nursing or protective brassieres. These two broad categories each comprise two general sub-categories, reusable pads and disposable pads, and, unitary brassieres and brassieres having replaceable absorbent pads. Each of the devices currently comprising these categories suffers from at least one disadvantage, including low moisture absorbency, visibility of the device through the clothing, bulkiness, inability to keep the moisture of the breast milk away from both the skin and clothing, poor fit within the brassiere, failure to maintain the proper shape within the brassiere, and, lack of multiple sizes for accommodating women's differently sized breasts. In addition, most of the devices available on the market are flat and when placed on the breast, they tend to bunch up around the edges. Most commercially available devices also only hold about one ounce of milk, so they can soak through in a matter of minutes when used by a nursing woman. Currently available devices also slide around easily within the brassiere and get out of position inside.

U.S. Pat. No. 5,690,536 issued to Madden, et al., discloses a disposable bra liner comprising three cup-shaped coextensive layers attached together with each layer presenting a circular periphery. The first layer is formed of a wicking material for wicking away moisture into the second absorbent layer which is attached to the outer surface of the first layer. The third moisture resistant layer is attached to the outer surface of the absorbent layer. The bra liners further include a structural member attached to the layers for maintaining the shape of the pad. The pad is shaped to fit on a particular shape breast. The structural member includes an elastic band attached to the layers at their peripheries and preferably has a plurality of spaced apart fold portions which taper inwardly from the band to present substantially V-shaped fold portion. Each layer preferably includes a plurality of similarly spaced fold apart portions formed therein. Fold apart portions allow the device to expand or be compressed to fit appropriately on any particular breast. The four layer construction is rather complicated. The complicated construction would result in a higher production cost of this device. Further, despite the V-shape fold portion which allow the device to extensively conform to different shape and size breasts, the device is limited in the range of sizes and shapes of breasts it could accommodate. Finally, the holding capacity of the device is limited to that of the absorbent layer. There is no provision for any reservoir or a device to hold excess fluids.

U.S. Pat. No. 5,611,086 issued to Eggen for a nursing garment discloses a nursing garment including a vest which is attached to an undergarment which covers the upper torso of the nursing mother. The device is a complete garment which, although it could be styled to be worn during the day, appears to be designed to be worn by a nursing mother at night. It would not be possible to wear this device under other clothing. The device includes an under garment with a pair of openings through which the breast protrude to permit nursing of the baby. The garment also includes a pair of flaps which may be connected together to cover the breasts. A sheet of liquid impervious, air permeable material is attached to the rearward surface of each flap and oriented to cover the breast. A sheet of liquid and air permeable material is attached over each sheet in the rearward surface of the flap to form a pocket between the cover sheet and sheet on each flap. A pad of liquid absorbent material is removably inserted into each pocket to absorb liquid which may leak from the nursing mother's breast. As stated in the Summary of the Invention, it is the general object of this invention to provide a garment for nursing mothers which permits them to rest or sleep without wearing a maternity bra or gown or bodice which fastens like a bra.

U.S. Pat. No. 5,683,286 issued to Kielland discloses a breast pad having absorbent portions and shaping portions. The absorbent portions include a center portion and a plurality of radially extending lobes. The shaping portions include a plurality of triangular sections that extend radially inward from the perimeter of the body to the center portion. This device incorporates divisions to account for the fact that the beast is not flat. It is capable of being shaped to conform to a woman's breast. The device includes an absorbing portion with three layers: 1. Substantially waterproof outer layer, described as being a thin layer of plastic; 2. An absorbent material, described as preferably being a material such a polyacrylate filler; and, 3. A permeable layer, described as being wood fiber product material which is in contact with the breast. The two-part construction (ie., the absorbent portion and the shaping portion) makes this device somewhat complicated to manufacture. In addition, the device is limited by the holding capacity of the absorbent portion. There is no provision made for a reservoir to hold excess liquid.

U.S. Pat. No. 4,164,228 issued to Weber-Unger discloses an absorbent pad for nursing brassieres. The device includes an extra thick lower portion disposed below the breast for providing additional storage capacity. The thicker lower portion would potentially present a problem with appearance, ie., the lower thicker portion would be apparent through clothing. In addition, the device does not include a waterproof material for preventing the liquid from leaking onto the wearer's clothing.

U.S. Design Pat. No. 246,729 issued to Murphy discloses an ornamental design for a combined breast shield and milk collector. As shown, the device appears to be a rigid device intended to allow for collection of breast milk. The device appears that it would be plainly visible under clothing, and would not allow for use outside of the home and without potential embarrassment to the user. As described, it appears to be a "breast milk collector". Hypothetically, the device could be used for collection of milk when the wearer is at home and does wish to use a pump. Since the patent is a design patent, there is very little description of the patent given. Accordingly, a primary object of the subject invention is to provide a disposable, multi-layer, bra liner for nursing women which includes a reservoir defined by an outer substantially waterproof layer and an inner substantially waterproof layer disposed about the periphery of the liner.

SUMMARY OF THE INVENTION

In view of the foregoing disadvantages inherent in the known types of nursing pad bra liners now present in the prior art, the present invention provides an improved nursing pad bra liner construction wherein the same can be utilized reliably in those situations where nursing pad bra liner are needed. As such, the general purpose of the present invention, which will be described subsequently in greater detail, is to provide a new and improved nursing pad bra liner which has all the advantages of the prior art nursing pad bra liners devices and none of the disadvantages.

To attain this, the present invention essentially comprises a multilayered design including a non-permeable layer for preventing transfer of breast milk from the liner to clothing, an absorbing layer for holding the milk within the liner and a wicking layer to draw the liquid away from the breast and into the absorbing layer. A non-permeable layer is also disposed about the outer periphery of the liner so that a reservoir is formed between the outer surface non-permeable layer and the layer on the periphery for retaining excess milk. An adhesive may be used to attache the non-permeable layer to the inside of the users bra cup to hold the liner in place. An adhesive may also be used to hold the bra liner to the breast. The design of the invention may incorporate cutouts along the periphery of the liner which allow the pad to more easily conform to the shape of a breast.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in this application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved nursing pad bra liner which may be easily and efficiently manufactured and marketed.

It is a further object of the present invention to provide a new and improved nursing pad bra liner which is of a reliable and durable construction.

An even further object of the present invention is to provide a new and improved nursing pad bra liner which is susceptible of a low cost of manufacture with regard to both materials and labor, and which accordingly is then susceptible of low prices of sale to the consuming public, thereby making such nursing pad bra liners economically available to the buying public.

Still another object of the present invention is to provide a new and improved nursing pad bra liner which provides some of the advantages of the prior art, while simultaneously overcoming some of the disadvantages normally associated therewith.

Another object of the present invention is to provide a new and improved nursing pad bra liner which is environmentally friendly for disposal.

Yet another object of the present invention is to provide a new and improved nursing pad bra liner which is comfortable for the user, conforms to the needed shape of the user without showing through outer garments, and stays in the desired location inside the bra.

Still another object of the present invention is to provide a new and improved nursing pad bra liner which provides for protection of outer garments from leakage and keeps the user dry.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front view of a nursing pad bra liner constructed in accordance with the present invention.

FIG. 2 is a back view of a nursing pad bra liner constructed in accordance with the present invention.

FIG. 3 is a sectional view along line 3—3 in FIG. 2.

DETAILED DESCRIPTION OF THE PREFERRED EMBODIMENTS

Referring to the drawings in detail and to FIGS. 1 and 2 in particular, reference character 10 generally designates a nursing pad bra liner constructed in accordance with the present invention. Bra liner 10 is initially a substantially flat oval shaped device to be inserted into the cup of a bra or into the clothing of the user. The bra liner generally comprises a front 12, a back 14, a top part 16, a bottom part 18, an outer periphery 20, and an inner periphery 22. It should be noted that the liner 10 is preferably for lining the interior of a bra, but may also be used without a bra if held in place by the user's clothing or by some other means such as an adhesive as discussed below.

The first layer 24 is generally a non-permeable material such as but not limited to plastic. The majority of the non-permeable material is the farthest away from the breast and in contact with the inside of the bra cup when the liner 10 is in use. Another preferred embodiment of the first layer 24 would be use of a semi-permeable material such as but not limited to neoprene or polyester which would prevent fluid from passing, but allow air to flow through the material. In this way any liquid leaking from the user's breast would be separated from the user's clothing, but air could pass through the liner thereby making the user more comfortable.

Referring to the drawings in detail and to FIG. 3 in particular, a second layer 26 is generally an absorbent material or multiple layers of an absorbent material such as but not limited to naturally absorbent materials such as cotton, cellulose, and the like. The absorbent material may also be made from other natural or synthetic materials such as but not limited silica gel, thermoplastic, copolymers, foam or similar materials. Many materials that contain or have been impregnated with a jelling agent such as but not limited to polyacrylate granted starch or maleic anhydride-based copolymers may be used to absorb the fluid. Some of the jelling agent impregnated materials will absorb the greatest amount of fluid with the least amount of expansion. Another preferred embodiment is using antibacterial agents or deodorant such as but not limited to backing soda in the absorbent second layer 26 to reduce odor from the fluid that accumulates.

A third layer 28 is generally a wicking material that would be a thin hydrophobic material which is liquid permeable and thus allows the fluid to wick through it to the absorbing second layer 26 while remaining dry and comfortable against the wearer's skin. This material may be similar, but not limited to, a stay-dry lining found in disposable diapers.

A reservoir 30 may be generally formed by two pieces with one piece comprising the first layer 24 on the front 12 of the bra liner 10 and a second piece generally comprising a donut shaped layer 25 placed on the back 14 of the bra liner 10. In this way, bunching or folds which will occur if the outer shell is simply folded around the absorbent material will be reduced or eliminated. The reservoir 30 extends from the outer periphery 20 to the the inner periphery 22 of the liner on the back as shown in FIG. 2. There should be a seal around the outer periphery 20 between the non-permeable or semi-permeable first layer 24 and the donut shaped layer 25 on the back 14 of the liner 10. These two, when sealed together, form a reservoir 30. Another preferred embodiment would be forming the reservoir 30 out of the first layer 24 by making it cup shaped with a lip portion forming the reservoir 30.

The liner 10 may have shape features to allow better conformity to the user. A preferred embodiment is generally wedge shaped cutouts 32 and 34. These cutouts 32 and 34 are generally defined along the outer periphery 20 of the liner 10. These cutaway portions 32 and 34 are in the shape of a V tapering inwardly toward the center of the liner. The cutaway portions 32 and 34 allow the liner to more naturally conform to the shape of a user's breast while not bunching around the outer periphery 20. These cutaway portions are preferably located on the top part 16 of the liner 10 to allow the liner 10 to conform to the natural shape of the breast. This permits the bottom part 18 to conform to the rounder portion of the lower breast and the top part 16 to conform to the upper portion of the breast to avoid bunching and folds and make a more complete seal between the outer periphery 20 and the entire breast.

The liner 10 may also include a means for attaching the liner 10 to an outer garment or inside a bra. A preferred embodiment is an adhesive material 36 disposed on the front 12 of the bra liner 10. The adhesive material 36 would insure that the liner 10 does not slide around within a bra or other undergarment. The liner 10 may also include a means for securing the liner 10 to the users breast with a preferred embodiment of placing adhesive material 38 to the back 14 of the liner 10. This would allow the liner 10 to be more firmly bonded to the user creating a seal which would provide greater protection from leaking fluid. Another preferred embodiment is placing lotion such as but not limited to skin cream with aloe, lanolin, or ointments to the back 14 of the liner 10 to help prevent skin irritation where the liner contacts the users breast.

It is to be understood that while certain forms of this invention have been illustrated and described, it is not limited thereto, except in so far as such limitations are included in the following claims and allowable functional equivalents thereof. Changes may be made in the combinations, operations and arrangements of the various parts and elements described herein without departing from the spirit and scope of the invention as defined in the following claims.

Operation of the Illustrated Embodiment

In operation, the invention 10 is placed inside the users bra cup with the waterproof layer 12 facing the bra cup. At the discretion of the user, the front 12 of the liner 10 may be attached to the inside of the bra cup with an adhesive 36 or even to the inner part of a garment if a bra is not desired. Also at the discretion of the user, the back 14 of the liner 10 may be attached to the breast with an adhesive 38. As seepage occurs, the fluid is passes into the liner 10 through the third wicking layer 28 and into the second absorbent layer 26. If and when the second absorbent layer 26 becomes saturated, the excess fluid will be retained inside the reservoir 30. The liner 10 is then thrown away after use.

I claim:

1. A liner for placing against the breast of a woman and for placing against the clothing of the woman, the liner being of the type to avert fluid leaking from the woman from soiling the woman's clothing, said liner comprising:

a layer of adsorbent material having an outside and an inside to absorb and hold at least some fluid leaking from a woman's breast when held there against;

a liquid impermeable outer layer for covering the outside of the absorbent material and extending inside partially around the absorbent material to form a reservoir;

wherein said liner has an oval shape, and wherein said liner has a top part and a bottom part and wherein said liner has an outer periphery, said liner further comprising a plurality of cutout portions in said liner said cutout portions generally having a wedge shape and extending from the outer periphery of the liner inward, for allowing the liner to form to the contour of a woman's breast.

2. The liner of claim 1 wherein said cutout portions are located in the top part of said liner.

3. The liner of claim 1 wherein said shell comprises a plurality of pieces connected together to prevent liquid from passing between said pieces.

4. The liner of claim 1 further comprising a wicking layer between the absorbent layer and the woman's breast when the liner is in use.

5. The liner of claim 1 wherein said cutout portions are generally V shaped.

6. The liner of claim 1 further comprising, an inner wicking layer to be placed against the user's breast.

7. The liner of claim 6 wherein more than one cutout portion is defined in the outer periphery of the liner and in the top portion of the liner.

8. The liner of claim 7 having an adhesive means on a portion of said liquid impermeable shell for affixing the liner to an undergarment.

9. The liner of claim 7 having an adhesive means on a portion of said liquid impermeable shell for affixing the liner to the breast of the user so that a seal is formed allowing liquid to be retained inside the bra liner.

10. A nursing pad bra liner comprising:
   an inner wicking layer having an outer periphery, an outside, and an inside, said inside to be placed against a user's breast when the liner is in use;
   an outer liquid impermeable layer for being placed in contact with the user's clothing, said liquid impermeable layer covering the outside of said wicking layer;
   an absorbent layer disposed between the liquid impermeable layer and the wicking layer for absorbing liquid; and
   wherein said liner has a top part and a bottom part and wherein said liner has an outer periphery, said liner further comprising, a plurality of notches in the top part of thereof, said liner notches generally having a wedge shape and extending from the outer periphery of the liner inward, for allowing the liner to form to the contour of a woman's breast.

11. The nursing pad bra liner of claim 10 further comprising a plurality of cutouts in the outer periphery of said liner to allow to the liner to generally form to the shape of a user's breast.

12. The nursing pad bra liner of claim 11 further comprising means on said liquid impermeable shell for attaching said liner to the user's clothing.

13. The nursing pad bra liner of claim 12 wherein said means on said liquid impermeable shell for attaching said liner to the user's clothing comprises adhesive.

14. The nursing pad bra liner of claim 12 wherein said means for attaching said liner to the user's breast comprises adhesive.

15. The nursing pad bra liner of claim 11 further comprising means for attaching said liner to the user's breast.

* * * * *